(12) United States Patent
Dupuis et al.

(10) Patent No.: US 8,703,098 B2
(45) Date of Patent: Apr. 22, 2014

(54) LABELLED ADRENOMEDULLIN DERIVATIVES AND THEIR USE FOR IMAGING AND THERAPY

(75) Inventors: Jocelyn Dupuis, Repentigny (CA); Alain Fournier, Pierrefonds (CA)

(73) Assignee: Institut de Cardiologie de Montreal, Montreal (CA)

( * ) Notice: Subject to any disclaimer, the term of this patent is extended or adjusted under 35 U.S.C. 154(b) by 1526 days.

(21) Appl. No.: 11/597,315

(22) PCT Filed: May 24, 2005

(86) PCT No.: PCT/CA2005/000791
§ 371 (c)(1),
(2), (4) Date: Nov. 21, 2006

(87) PCT Pub. No.: WO2005/116065
PCT Pub. Date: Dec. 8, 2005

(65) Prior Publication Data
US 2008/0274050 A1    Nov. 6, 2008

Related U.S. Application Data

(60) Provisional application No. 60/573,334, filed on May 24, 2004.

(51) Int. Cl.
*A61K 51/00* (2006.01)
*A61M 36/14* (2006.01)

(52) U.S. Cl.
USPC ........................................ 424/1.65; 424/1.69

(58) Field of Classification Search
USPC ...................................................... 424/1.69
See application file for complete search history.

(56) References Cited

PUBLICATIONS

Hasegawa et al. (Acta Histochem. Cytochem. 1998, 31, 335-343).*
Wimalawansa (Crit. Rev. Neurobiol. 1997, 11, 167-239; see abstract).*
Kakishita et al. (Clinical Sci. 1999, 96, 33-39).*
Kitamura, K. et al. (1994) Cloning and Characterization of CDNA Encoding a Precursor for Human Adrenomedullin. Biochem. Biophys. Res. Commun. 194, 720-725 Jun. 1993.
Sugo, S., Minamino, N., Kangawa, K. et al. (1994) Endothelial Cells Actively Synthesize and Secrete Adrenomedullin. Biochem. Biophys. Res. Commun. 201, 1160-1165 Jun. 1994.
Hinson, J. P., Kapas, S. and Smith, D. M. (2000) Adrenomedullin, a Multifunctional Regulatory Peptide.Endocr. Rev. 21, 138-167 Apr. 2000.
Hay, D. L. and Smith, D. M. (2001) Receptors: Molecular Identity and Function. Peptides 22, 1753-1763 Jun. 2001.
Kuwasako, K., Kitamura, K., Ito, K. et al. (2001) The Seven Amino Acids of Human RAMP2 . J. Biol. Chem. 276, 49459-49465 Oct. 2001.
Poyner, D. R., Sexton, P. M., Marshall, I. et al. (2002) International Union of Pharmacology, XXXII. The Mammalian. Pharmacol. Jun. 2002 Rev. 54, 233-246.
Eguchi, S., Hirata, Y., Iwasaki, H. et al. (1994) Structure-Activity Relationship of Adrenomedullin, a Novel Vasodilatory Peptide. Endocrinolog 135, 2454-2458 Jul. 1994.
Hirayama, N., et al. (1999) Secretion and Clearance of the Mature Form of Adrenomedullin in Humans. Life Sci. 64, 2505-2509 Mar. 1999.
Nishikimi, T., Kitamura, K., Saito, Y. et al. (1994) Clinical Studies on the Sites of Production and Clearance of Circulating. Hypertension 24, 600-604 Jul. 1994.
Nishikimi, T., Matsuoka, H., Shimada, K., Matsuo, H. and Kangawa, K. (2004) Production and Clearance Sites . Plasma.Am. J. Hypertens. 13,1032-1034 Sep. 2000.
Nishikimi, T. et al. (2001) the Active Molecular Form of Plasma Adrenomedullin is Extracted. Clin. Sci. 100, 61-66 Sep. 2000.
Dupuis, J., Goresky, C. A. and Fournier, A. (1996) Pulmonary Clearance of Circulating Endothelin-1 in Dogs in Vivo. J. Appl. Physiol. 81, 1510-1515 May 1996.
Kitamura, K., Kato, J., Kawamoto, M. et al. (1998) the Intermediate Form of Glycine-Extended Adrenomedullin. Biochem. Biophys. Res. Commun. 244, 551-555 Feb. 1998.
Martinez, A., Miller, M. J., Catt, K. J. and Cuttitta, F. (1997) Adrenomedullin Receptor Expression in Human Lung and in Pulmonary. J. Histochem. Cytochem. 45, 159-164 Oct. 1996.
Owji, A. A., Smith, D. M., Coppock, H. A. et al. (1995) An Abundant and Specific Binding Site for the Novel Vasodilator Adrenomedullin. Endocrinology 136,May 1995 2127-2134.
Poyner, D. R. (1997) Molecular Pharmacology of Receptors for Calcitonin-Gene-Related Peptide, Amylin and Adrenomedullin. Biochem. Soc. Trans. 25, 1032-1036 Mar. 1997.
Dschietzig, T., Azad, H. A., Asswad, L., Bohme, C., Bartsch, C. and Baumann, G. (2002) The Adrenomedullin Receptor Acts . Biochem. Biophys. Res. Commun. 294, 315-318 Apr. 2002.
Qing, X. Svaren, J. et al (2001) MRNA Expression of Novel CGRP1 Receptors and Their Activity-. Am. J. Physiol. Lung Cell. Mol. Physiol. 280, L547-L554 Oct. 2000.
Nagae, T., Mukoyama, M., Sugawara, A. et al. (2000) Rat Receptor-Activity-Modifying Proteins (RAMPS). Biochem. Biophys. Res. Commun. 270,89-93 Feb. 2000.
Hagner, S., Haberberger, R., Hay, D. L. et al. (2003) Immunohistochemical Detection of the Calcitonin Receptor-Like Receptor. Eur. J. Pharmacol. 481, 147-151 Sep. 2003.
Hagner, S., Stahl, U., Knoblauch, B., McGregor, G. P. and Lang, R. E. (2002) Calcitonin Receptor-Like Receptor. Cell Tissue Res. 310, 41-50 Aug. 2002.

(Continued)

*Primary Examiner* — Michael G Hartley
*Assistant Examiner* — Melissa Perreira
(74) *Attorney, Agent, or Firm* — James A. Sheridan; Sheridan Law, LLC (57) ABSTRACT

The present invention relates to an adrenomedullin derivative including an adrenomedullin peptide chelated with at least one active agent. Examples of active agents include a paramagnetic element, a radioactive element and a fibrinolytic agent, among others. Paramagnetic agents have a distribution that is relatively easily shown through Magnetic Resonance Imaging (MRI). Radioactive agents have applications in imaging and delivery of radiations, depending on the specific element included in the active agent. Delivery of fibrinolytic agents mainly to a specific organ, such us for example to the lungs, allows to substantially improve the specificity and efficacy of thrombolytic therapy by allowing local delivery of the fibrinolytic agent, thereby reducing the risks of major bleeding in the therapy of the organ. If the organ is the lungs, a non-limiting example of pathology treatable with the fibrinolytic is pulmonary embolus.

14 Claims, 8 Drawing Sheets

(56) References Cited

PUBLICATIONS

Dilworth, J. R. and S. J. Parrott (1998). "The Biomedical Chemistry of Technetium and Rhenium." Chem. Soc. Rev. 27: 43-55. Aug. 1997.

Dupuis, J., A. Caron, et al. (2005). "Biodistribution, Plasma Kinetics and Quantification of Single Pass Pulmonary Clearance of Adrenomedullin." Clin Sci 1: Mar. 1, 2005.

Hom, R. K. and J. A. Katzenellenbogen (1997). "Technetium-99M-Labelled Receptor-Specific Small-Molecule." Nucl Med Biol 24(6): 485-98. Apr. 1997.

Kitamura, K., J. Sakata, et al. (1993). "Cloning and Characterization of CDNA." Biochem Biophys Res Commun 194(2): 720-5. Jun. 1993.

Liu, S. and D. S. Edwards (1999). "99MTC-Labelled Small Peptides as Diagnostic Radiopharmaceuticals." Chem Rev 99(9): 2235-68. May 1999.

Forest, M. & Fournier, A.: BOP Reagent for the Coupling of PGLU and BOC HIS (TOS) in Solid Phase. Inter. Journal of Peptide and Protein Research, 1990; 35: 89-94 Jul. 1989.

Hinson, Joy Patricia et al. Adrenomedullin, A Multifunctional Regulatory Peptide. Endocrine Society vol. 21 No. 2 138-167 Sep. 2006 USA.

Naoteru Hirayama etal Secretion and Clearance of the Mature Form . . . Elsevier Science Inc. vol. 64 No. 26 2505-2509 Mar. 1999 Japon.

T. Nishikimi et al Clinical Studies on the Sites of Production and Clearance . . . American Heart Ass. 1994;24 600-604 1994. USA.

Toshio Nishikimi et al Production and Clearance Sites of Two Molecular Forms of Adrenomedullin in Human Plasma Elsevier Science Inc. vol. 13 No. 9 1032-1034 Sep. 2000 USA.

Toshio Nishikimi et al The Active Molecular Form of Plasma Adrenomedullin Is Extracted in the Pulmonary . . . The Biocheminal Society. Clinical Science (2001) 61-66 Sep. 2000 JP.

Shin Sugo et al Endothelial Cells Actively Synthesize and Secrete Adrenomedullin Biochemical and Biophysical Research Comm. vol. 21 No. 3 1160-1166 Jun. 1994 JP.

\* cited by examiner

Pulmonary kinetics of $^{125}$I-rAM1-50 in dogs

A) Control

B) After injection of cold rAM1-50

Figure 9

SEQUENCE LISTING

```
<160> NUMBER OF SEQ ID NOS: 2

<210> SEQ ID NO 1
<211> LENGTH: 52
<212> TYPE: PRT
<213> ORGANISM: Artificial
<220> FEATURE:
<223> OTHER INFORMATION: synthetic peptide

<400> SEQUENCE: 1

Tyr Arg Gln Ser Met Asn Asn Phe Gln Gly Leu Arg Ser Phe Gly Cys
1               5                   10                  15

Arg Phe Gly Thr Cys Thr Val Gln Lys Leu Ala His Gln Ile Tyr Gln
            20                  25                  30

Phe Thr Asp Lys Asp Lys Asp Asn Val Ala Pro Arg Ser Lys Ile Ser
        35                  40                  45

Pro Gln Gly Tyr
    50

<210> SEQ ID NO 2
<211> LENGTH: 31
<212> TYPE: PRT
<213> ORGANISM: Artificial
<220> FEATURE:
<223> OTHER INFORMATION: synthetic peptide

<400> SEQUENCE: 2

Thr Val Gln Lys Leu Ala His Gln Ile Tyr Gln Phe Thr Asp Lys Asp
1               5                   10                  15

Lys Asp Asn Val Ala Pro Arg Ser Lys Ile Ser Pro Gln Gly Tyr
            20                  25                  30
```

LABELLED ADRENOMEDULLIN DERIVATIVES AND THEIR USE FOR IMAGING AND THERAPY

This application claims priority from U.S. Provisional Patent Application Ser. No. 60/573,334 filed May 24, 2004.

FIELD OF THE INVENTION

The present invention relates to the use of labelled compounds for imaging or therapy. More specifically, the present invention is concerned with labelled adrenomedullin derivatives and their use for imaging and therapy.

BACKGROUND OF THE INVENTION

A currently existing agent for the clinical imaging of pulmonary circulation is $^{99m}$Tc-labelled albumin macroaggregates. This agent is used for the diagnosis of physical defects of the circulation due to pulmonary embolus. This agent is larger than small pulmonary vessels. Accordingly, further to being injected in an animal, this agent is trapped by these small pulmonary vessels, which enables external detection.

Important limitations of albumin macroaggregates include the inability to image the small pulmonary circulation beyond the point of obstruction. This limits the sensitivity of this substance to detect small vascular defects. Also; there are potential infectious risks since albumin macroaggregates are derived from human albumin. Additionally, albumin macroaggregates are unable to detect functional (biological) defects of the pulmonary circulation since their retention is uniquely dependent on physical characteristics of the vessels.

There also exist compounds that have an affinity for particular organs, such as for example adrenomedullin (AM). AM is a 52-amino-acid multifunctional regulatory peptide highly expressed in endothelial cells and widely distributed in various tissues [1,2]. The structure of AM is well conserved across species, with only six substitutions and two deletions in the rat [rAM(1-50)] compared with the human [hAM(1-52)] [3]. AM possesses structural homology with CGRP (calcitonin gene-related peptide), making it a member of the calcitonin/CGRP/amylin family (CT/CGRP/AMY peptide family.

The biological activities of AM are mediated by receptors composed of two essential structural components: a seven-transmembrane protein, the calcitonin receptor-like receptor (CRLR), and a single transmembrane domain termed RAMP (receptor-activity-modifying protein) [4,5]. The association of CRLR/RAMP1 represents the CGRP1 receptor and is not specific to AM. At the opposite, a specific AM receptor comes from the coupling of CRLR/RAMP2 or CLRL/RAMP3 [6]. This specific AM receptor can be blocked by the C-terminal AM fragment [hAM(22-52)] [7].

A biological action of AM is a potent hypotensive effect. The systemic hypotensive action of AM can however be reduced and sometimes abolished after intravenous compared with intra-arterial infusion [8], suggesting that the lungs have a potential to clear circulating AM and modulate its circulating levels. Many studies have confirmed that AM is cleared by the pulmonary circulation [9-12]. However, the relative contribution of the lungs to AM clearance in comparison with other organs has not been systematically evaluated and, more specifically, single-pass pulmonary clearance of AM has not been quantified in vivo.

Against this background, there exists a need in the industry to provide novel compounds having an affinity for the lungs, and more specifically to provide such compounds suitable for use in therapy and imaging.

The present description refers to a number of documents, the content of which is herein incorporated by reference in their entirety.

OBJECTS OF THE INVENTION

An object of the present invention is therefore to provide novel compounds having an affinity for the lungs.

SUMMARY OF THE INVENTION

In a first broad aspect, the invention provides an adrenomedullin derivative comprising an adrenomedullin peptide chelated to at least one active agent. For example, the adrenomedullin derivative comprises adrenomedullin having the sequence: Tyr-Arg-Gln-Ser-Met-Asn-Asn-Phe-Gln-Gly-Leu-Arg-Ser-Phe-Gly-Cys-Arg-Phe-Gly-Thr-Cys-Thr-Val-Gln-Lys-Leu-Ala-His-Gln-Ile-Tyr-Gln-Phe-Thr-Asp-Lys-Asp-Lys-Asp-Asn-Val-Ala-Pro-Arg-Ser-Lys-Ile-Ser-Pro-Gln-Gly-Tyr (SEQ ID 1), or a fragment thereof. Examples of active agents include active agents comprising at least one paramagnetic element, active agents comprising at least one radioactive element, and fibrinolytic agents, among others.

The biodistribution, pharmacokinetics and multi-organ clearance of AM were evaluated in rats and its single-pass pulmonary clearance was measured in dogs by the indicator-dilution technique. Intravenously administered $^{125}$I-rAM(1-50) [rat AM(1-50)] was rapidly cleared following a two-compartment model with a relatively rapid distribution half-life of 2.0 min [95% Cl (confidence interval), 1.98-2.01] and an elimination half-life of 15.9 min (95% Cl, 15.0-16.9). The lungs retained most of the injected activity with evidence of single-pass clearance, since retention was lower after intra-arterial (13.5±0.6%) compared with intravenous (30.4±1.5%; P<0.001) injection. Lung tissue levels of total endogenous AM were about 20-fold higher than in other organs with no difference in plasma levels across the pulmonary circulation. In dogs, there was 36.4±2.1% first-pass unidirectional extraction of $^{125}$I-rAM(1-50) by the lungs that was reduced to 21.9±2.4% after the administration of unlabelled rAM(1-50) (P<0.01). Extraction was not affected by calcitonin gene-related peptide administration (40.6±2.9%), but slightly reduced by the C-terminal fragment of human AM(22-52) (31.4±3.3%; P<0.01). These data demonstrate that the lungs are a primary site for AM clearance in vivo with approximately 36% first-pass extraction through specific receptors. This suggests that the lungs not only modulate circulating levels of this peptide, but also represent one of its primary targets.

In addition, a chelated human AM derivative (hAM-1-52) was developed using diethylenetriaminepentaacetic acid (DTPA) radiolabelled with $^{99m}$Tc. The biodistribution, plasma kinetics and utility of $^{99m}$Tc-DTPA-hAM1-52 as a pulmonary vascular imaging agent were evaluated.

After HPLC purification, the radiochemical purity of $^{99m}$Tc-DTPA-hAM1-52 was 92.0±2.3%. A hemodynamically inactive dose of the compound was intravenously injected to anesthetized dogs (n=6) and the tracer activity serially determined in blood samples as well as in various regions of interest using external detection with a gamma camera. In additional experiments, the capacity to image perfusion defects was evaluated after selective surgical pulmonary lobectomy.

$^{99m}$Tc-DTPA-hAM1-52 was relatively rapidly cleared from plasma following a two-compartment model with a relatively rapid distribution half-life of 1.75 min (95% confidence interval, Cl: 1.31-2.65). The lungs retained most of the injected activity after 30 minutes (27.0±2.7%, p<0.001), as compared to kidneys (19.2±3.1%), liver (11.7±1.4%), heart (7.2±2.0%), bladder (5.7±1.7%) and gallbladder (1.0±0.4%). Lung retention was mildly reduced with time but sustained up to 4 hours after the injection (15.8±2.3%), while uptake progressively increased in the bladder (26.8±4.3%) and gallbladder (5.50±2.6%). After selective pulmonary lobectomy, anatomically corresponding perfusion defects were easily detectable by external imaging. Therefore, chelated AM derivatives display important and extended lung retention and are promising new agents for pulmonary vascular imaging. Their use can image anatomical perfusion defects, but also has the inherent potential for the detection functional vascular perfusion abnormalities.

Advantageously, AM has a potential to image the small pulmonary circulation. Also by its nature, AM allows a functional imaging of the pulmonary circulation, which is advantageous for some diagnostic purposes.

In addition, AM is a physiological endogenous peptide used in tracer amounts. At those concentrations, AM is devoid of any significant biological activity. Furthermore, risks of infection are reduced in using AM instead of albumin macroaggregates for pulmonary imaging.

In a second broad aspect, the invention provides a method of detecting the presence or absence of pulmonary embolus in a mammal. The method comprises:
   administering to the mammal a labelled adrenomedullin derivative in an amount and for a duration effective to achieve binding between the labelled adrenomedullin derivative and pulmonary adrenomedullin-receptor-bearing cells;
   generating an image of the distribution of the labelled adrenomedullin derivative in the lungs of said mammal; and
   detecting the presence or absence of pulmonary embolus.

In a third broad aspect, the invention provides a method of detecting the presence and density of adrenomedullin receptor-bearing cells in a mammal comprising:
   administering to the mammal a labelled adrenomedullin derivative for a time and under conditions effective to achieve binding between the labelled adrenomedullin derivative and adrenomedullin-receptor-bearing cells, and
   determining the distribution of the labelled adrenomedullin derivative for a time and under conditions effective to obtain an image of the mammal.

In a fourth broad aspect, the invention provides a method of delivering at least one active agent to pulmonary adrenomedullin-receptor-bearing cells in a mammal, the method comprising administering to the mammal an adrenomedullin derivative chelated to the active agent in an amount and for a duration effective to achieve binding between the adrenomedullin derivative and the pulmonary adrenomedullin-receptor-bearing cells.

If the active agent includes a fibrinolytic agents, chelation of fibrinolytic agents to AM derivatives has the potential to substantially improve the specificity and efficacy of thrombolytic therapy by allowing local delivery of the fibrinolytic agent, thereby reducing the risks of major bleeding in the therapy of pulmonary embolus.

In a fifth broad aspect, the invention provides a use of labelled adrenomedullin derivatives to image the lungs of a mammal.

Other objects, advantages and features of the present invention will become more apparent upon reading of the following non-restrictive description of preferred embodiments thereof, given by way of example only with reference to the accompanying drawings.

DETAILED DESCRIPTION

The present invention relates to the use of an adrenomedullin derivative including an adrenomedullin peptide chelated to at least one active agent. For example, the adrenomedullin peptide comprises adrenomedullin having the sequence: Tyr-Arg-Gln-Ser-Met-Asn-Asn-Phe-Gln-Gly-Leu-Arg-Ser-Phe-Gly-Cys-Arg-Phe-Gly-Thr-Cys-Thr-Val-Gln-Lys-Leu-Ala-His-Gln-Ile-Tyr-Gln-Phe-Thr-Asp-Lys-Asp-Lys-Asp-Asn-Val-Ala-Pro-Arg-Ser-Lys-Ile-Ser-Pro-Gln-Gly-Tyr (SEQ ID NO:1), or a fragment thereof. This adrenomedullin peptide corresponds to amino acids 1-52 of human adrenomedullin. Additionally, fragments of adrenomedullin correspond to shorter peptide sequences, such as amino acids 1-50 of rat adrenomedullin.

Examples of active agents include a paramagnetic element, a radioactive element and a fibrinolytic agent, among others. Paramagnetic agents have a distribution that is relatively easily shown through Magnetic Resonance Imaging (MRI). Radioactive agents have applications in imaging and delivery of radiations, depending on the specific element included in the active agent. Delivery of fibrinolytic agents mainly to a specific organ, such as for example to the lungs, allows to substantially improve the specificity and efficacy of thrombolytic therapy by allowing local delivery of the fibrinolytic agent, thereby reducing the risks of major bleeding in the therapy of the organ. If the organ is the lungs, a non-limiting example of pathology treatable with the fibrinolytic is pulmonary embolus Non-limiting examples of radioactive elements suitable for imaging include: $^{99m}$Tc, $^{111}$In, $^{67}$Ga, $^{64}$Cu, $^{90}$Y, $^{161}$Tb, $^{177}$Lu, and $^{111}$In. Such agents may be compelxed directly into the adrenomedullin molecule or related derivative or chelated to the adrenomedullin related peptide through a chelator selected from: diethylenetriaminepentaacetic acid (DTPA), 1,4,7,10-tetraazacyclododecan-N,N',N'',N'''-tetraacetic acid (DOTA), 1,4,8,11-tetraazacyclotetradecane-N,N',N'',N'''-tetraacetic acid (TETA), and 6-hydrazinonicotinamide (HYNIC), among others.

Imaging allows, for example, detecting the presence or absence of pulmonary embolus in a mammal, for example in a human. To that effect a labelled adrenomedullin derivative is administered to the mammal in an amount and for a duration effective to achieve binding between the labelled adrenomedullin derivative and pulmonary adrenomedullin-receptor-bearing cells. Then, an image of the distribution of the labelled adrenomedullin derivative in the lungs of the mammal is generated. Subsequently, the presence or absence of pulmonary embolus is detected.

In a non-limiting example of implementation, the radiolabelled adrenomedullin derivative is administered to the mammal through injection of from about 0.1 nmol to about 100 nmol of 99mTc-AM-DTPA. In another non-limiting example of implementation, the radiolabelled adrenomedullin derivative is administered to the mammal through injection of from about 0.5 mCi to about 500 mCi of 99mTc-AM-DTPA. However, it is within the scope of the invention to inject any other suitable amount of the labelled adrenomedullin derivative and to administer the labelled adrenomedullin derivative using any other suitable method.

In some embodiments of the invention, the labelled adrenomedullin derivative is detected to produce a model of the distribution of labelled adrenomedullin in the lungs. Then, the model of the lungs indicates the presence of a likely pulmonary embolus through the presence of a reduced activity region within the model. The reduced activity region is a region of the model of the lungs wherein a concentration of labelled adrenomedullin is substantially reduced with respect to adjacent regions of the model of the lungs.

In other examples, the adrenomedullin derivative comprises an element selected from: Fe, Ca, Mn, Mg, Cu, and Zn. These elements have applications, among other examples of application, to ion depletion therapy for cancer and other pathologies. In these cases, non-limitative examples of suitable chelating agents used for binding the element to adrenomedullin include desferoxamine and N,N',N''-tris(2-pyridylmethyl)-cis-1,3,5-triaminocyclohexane (tachpyr).

In other embodiments of the invention, a method of detecting the presence and density of adrenomedullin receptor-bearing cells in a mammal is provided. This method includes:
administering to the mammal a labelled adrenomedullin derivative for a time and for a duration effective to achieve binding between the labelled adrenomedullin derivative and adrenomedullin-receptor-bearing cells, and
determining the distribution of the labelled adrenomedullin derivative for a time and for a duration effective to obtain an image of the mammal.
In other methods, at least one active agent is delivered to pulmonary adrenomedullin-receptor-bearing cells in a mammal.

EXAMPLE 1

A Process to Produce $^{99m}$Tc-Labelled AM

In this example, the adrenomedullin produced is a human adrenomedullin having the sequence:

```
                                            (SEQ ID 1)
H-Tyr-Arg-Gln-Ser-Met-Asn-Asn-Phe-Gln-Gly-Leu-Arg-

Ser-Phe-Gly-Cys-Arg-Phe-Gly-Thr-Cys-Thr-Val-Gln-

Lys-Leu-Ala-His-Gln-Ile-Tyr-Gln-Phe-Thr-Asp-Lys-

Asp-Lys-Asp-Asn-Val-Ala-Pro-Arg-Ser-Lys-Ile-Ser-

Pro-Gln-Gly-Tyr-CONH₂
```

However, it is within the scope of the invention to use any other suitable adrenomedullin, such as rat adrenomedullin or derivatives of the CT/CGRP/AMY peptide family, as well as their modified products such as those obtained after N- and/or C-terminal substitution.

A method for synthesizing an a CT/CGRP/AMY peptide suitable for use with the present invention, such as for example adrenomedullin, was performed as follows. The following commercial N-α-fluorenylmethyloxycarbonyl [Fmoc]-L-amino acids were used: Alanine [Fmoc-Ala], Arginine-N$^\omega$-(2,2,4,6,7-pentamethyldihydrobenzofuran-5-sulfonyl) [Fmoc-Arg(Pbf)], Asparagine-N$^{65}$-trityl [Fmoc-Asn (Trt)], Aspartic acid-α-t-butyl ester [Fmoc-Asp(OtBu)], Cysteine-S-trityl [Fmoc-Cys(Trt)], Glutamine-N$^\delta$-trityl [Fmoc-Gln(Trt)], Glycine [Fmoc-Gly], Histidine-N$^{im}$-trityl [Fmoc-His(Trt)], Isoleucine [Fmoc-Ile], Leucine [Fmoc-Leu], Lysine-N$^\epsilon$-t-butyloxycarbonyl [Fmoc-Lys(Boc)], Methionine [Fmoc-Met], Phenylalanine [Fmoc-Phe], Proline [Fmoc-Pro], Serine-O-t-butyl [Fmoc-Ser(tBu)], Threonine-O-t-butyl [Fmoc-Thr(tBu)], Tyrosine-O-t-butyl [Fmoc-Tyr (tBu)] and Valine [Fmoc-Val].

Adrenomedullin and its CT/CGRP/AMY analogues were synthesized, using a solid phase procedure based on the Fmoc-amino acid chemistry—BOP reagent (benzotriazol-1-yl-oxy-tris(dimethylamino)-phosphonium hexafluorophosphate) coupling strategy. This procedure is better described in reference 35, which is hereby incorporated by reference.

In summary, a Fmoc-Rink-amide-acetamidonorleucylaminomethyl resin (4-(2',4'-dimethoxyphenyl-Fmoc-aminomethyl)-phenoxy-acetamidonorleucylaminomethyl resin) was used as the solid support. After a treatment with a 20% piperidine (Pip)-dimethylformamide (DMF) mixture, in order to remove the protecting Fmoc moiety and free the amine anchor on the solid support, the first amino acid of the synthesis, corresponding to the last residue of the peptide sequence (Tyrosine), was coupled to the resin with BOP reagent, in the presence of diisopropylethylamine (DIEA). In function of the resin substitution, a ratio of 3 equivalents (eq) of Fmoc-amino acid, 3 eq of BOP and 5 eq of DIEA was used for each coupling step and each step was monitored using a ninhydrin test.

After the complete synthesis of the peptide chain, a final Fmoc deprotection step was carried out with 20% Pip/DMF. For derivatives containing a N-terminal chelating functional, the resin-bound peptide was transferred into a round-bottom flask and the incorporation of a N-substituting moiety (examples of such moieties include, but are not limited to, diethylenetriaminepentaacetic acid (DTPA) or 1,4,7,10-tetraazacyclododecan-N,N',N'',N'''-tetraacetic acid (DOTA) or 1,4,8, 11-tetraazacyclotetradecane-N,N',N'',N'''-tetraacetic acid (TETA or 6-hydrazinonicotinamide (HYNIC), among others) was achieved by mixing the resin-adrenomedullin overnight, at 50° C., with 3 eq of the substituting compound, 3 eq of BOP reagent and 3 eq of DIEA dissolved in a solvent mixture of DMF—dichloromethane—dimethylsulfoxide (49%:49%:2%).

The peptide was finally cleaved from the resin using a mixture of trifluoroacetic acid (TFA)—ethanedithiol (EDT)—phenol—$H_2O$ (9.5 mL-0.25 mL-0.3 g-0.25 mL; 10 mL/g of resin) for 2 hours, at room temperature. After TFA evaporation, the crude material was precipitated and washed using diethylether. The peptide was then dried and kept at −20° C. until cyclization and purification.

AM cyclization, purification and characterization was performed, as follows. Crude adrenomedullin (AM) (200 mg) was dissolved in a 2 mL solution of 50% dimethylsulfoxide/$H_2O$ in order to generate the disulfide bridge between the cysteine side-chains. After 30 min at room temperature, the peptide solution was diluted with 500 mL of 10% acetonitrile (ACN) in aqueous TFA (0.06%) before being injected onto a RP-HPLC $C_{18}$ (15 µm; 300 Å) column (250×21.20 mm) (Jupiter column from Phenomenex, Torrance, Calif.). The purification step was carried out using a Waters Prep 590 pump system connected to a Waters Model 441 absorbance detector. The flow rate was fixed at 20 mL/min and the peptide was eluted with a solvent gradient of 0% to 100% solvent B, in 2 h, where solvent A is 10% ACN in aqueous TFA (0.06%) and solvent B is 45% ACN in aqueous TFA (0.06%).

The homogeneity of the various fractions was evaluated using analytical RP-HPLC with a $C_{18}$ (5 µm; 300 Å) column (250×4.60 mm) ((Jupiter column from Phenomenex, Torrance, Calif.) connected to a Beckman 128 solvent module coupled to a Beckman 168 PDA detector. The flow rate was 1.0 mL/min and the elution of the peptide was carried out with a linear gradient of 20 to 60% B, where A is TFA 0.06% and B is ACN. Aliquots of 20 µl were injected and analyzed. Homogeneous fractions were pooled, lyophilized and then analyzed again by analytical HPLC, and by MALDI-TOF mass spectrometry (Voyager DE spectrometer—Applied Biosystems, Foster City, Calif.) using α-cyano-4-hydroxycinnamic acid as a matrix for peptide inclusion and ionization.

Labeling of a chelating adrenomedullin derivative (exemplified with DTPA—AM and $^{99m}$technetium) was as follows. The substituted peptide DTPA—AM (18.5 µg-2.89 nmol) was dissolved in 1 mM HCl (100 µl) and then, $SnCl_2.2H_2O$ (14.8 µl of a 0.2 mg/mL aqueous solution: 3 µg-13 nmol) was added, followed immediately with $Na^{99m}TcO_4$ (15 mCi-28.9 pmol) in saline. After 1 h at room temperature, the solution was diluted with 1 mL of phosphate buffer—saline (PBS) at pH 7.4.

In other examples, adrenomedullin (AM) or AM fragments or AM analogues are modified with agents able to bind radioactive and/or paramagnetic chemical elements such as those from the following non limiting list: $^{99m}$technetium ($^{99m}$Tc), $^{111}$indium ($^{111}$In), $^{67}$gallium ($^{67}$Ga), $^{64}$copper ($^{64}$Cu), among others. In the present case, the modified AM, AM fragment or AM analogue is particularly suitable, but non-limitatively, for imaging with for instance, a gamma camera, a positron emission tomography camera, a magnetic resonance instrument, or any other suitable imaging device.

In other examples, adrenomedullin (AM) or AM fragments or AM analogues are modified with agents able to bind radioactive elements such as those from the following non exclusive list: $^{90}$yttrium ($^{90}$Y), $^{161}$terbium ($^{161}$Tb), $^{177}$lutetium ($^{177}$Lu), $^{111}$indium ($^{111}$In), among others. In this case, the modified AM, AM fragment or AM analogue are particularly suitable, but non-limitatively, for application in radiotherapy.

In other examples, adrenomedullin (AM) or AM fragments or AM analogues are modified with agents able to bind ions such as those produced from the elements appearing in the following non limiting list: iron (Fe), calcium (Ca), manganese (Mn), magnesium (Mg), copper (Cu), and zinc (Zn), among others. In the present case, the modified AM, AM fragment or AM analogues are particularly suitable, but non-limitatively, for application in chemotherapy, using, for example, an intracellular ion depletion strategy. In this particular case, possible chelating agents for ion depletion are selected form the following non-limiting list: desferioxamine, tachpyr (N,N',N''-tris(2-pyridylmethyl)-cis-1,3,5-triaminocyclohexane), among others.

While a specific process for producing a labeled adrenomedullin derivative according to the invention is described hereinabove, the reader skilled in the art will readily appreciate that it is within the scope of the invention to produce labeled adrenomedullin derivatives that are within the scope of the claimed invention in any other suitable manner.

EXAMPLE 2

Pharmacokinetics of $^{125}$I Labelled AM in Rats

Introduction

This example was designed to evaluate the biodistribution, pharmacokinetics and multiorgan clearance of AM in rats in vivo. Quantification of single-pass pulmonary kinetics of AM and its mechanism was characterized further in dogs using the single bolus indicator-dilution technique.

Methods

All experimental procedures were performed in accordance with the regulations and ethical guidelines from Canadian Council for the Care of Laboratory Animals, and received approval by the Animal Ethics and Research Committee of the Montreal Heart Institute. Male Sprague-Dawley rats (Charles River), weighing between 400-450 g, were anaesthetized by an initial intramuscular dose of xylazine (10 mg/kg of body weight) and ketamine (50 mg/kg of body weight), followed by an intra-peritoneal injection of heparin (2000 units; Sigma). Catheters were inserted into the right carotid artery and jugular vein. Heart rate and systemic blood pressure were monitored continuously. Additional doses of xylazine/ketamine were used if noxious stimuli (pinching the hind feet) elicited nociceptive motor reflexes or changes of the systemic blood pressure. Venous and arterial blood samples (3 ml) were collected and centrifuged (1875 g, 15 min, 4° C.) and the plasma saved for subsequent measurement of irAM (immunoreactive AM). A similar amount of saline was infused into the animals to prevent hypovolaemia.

Figure 1:
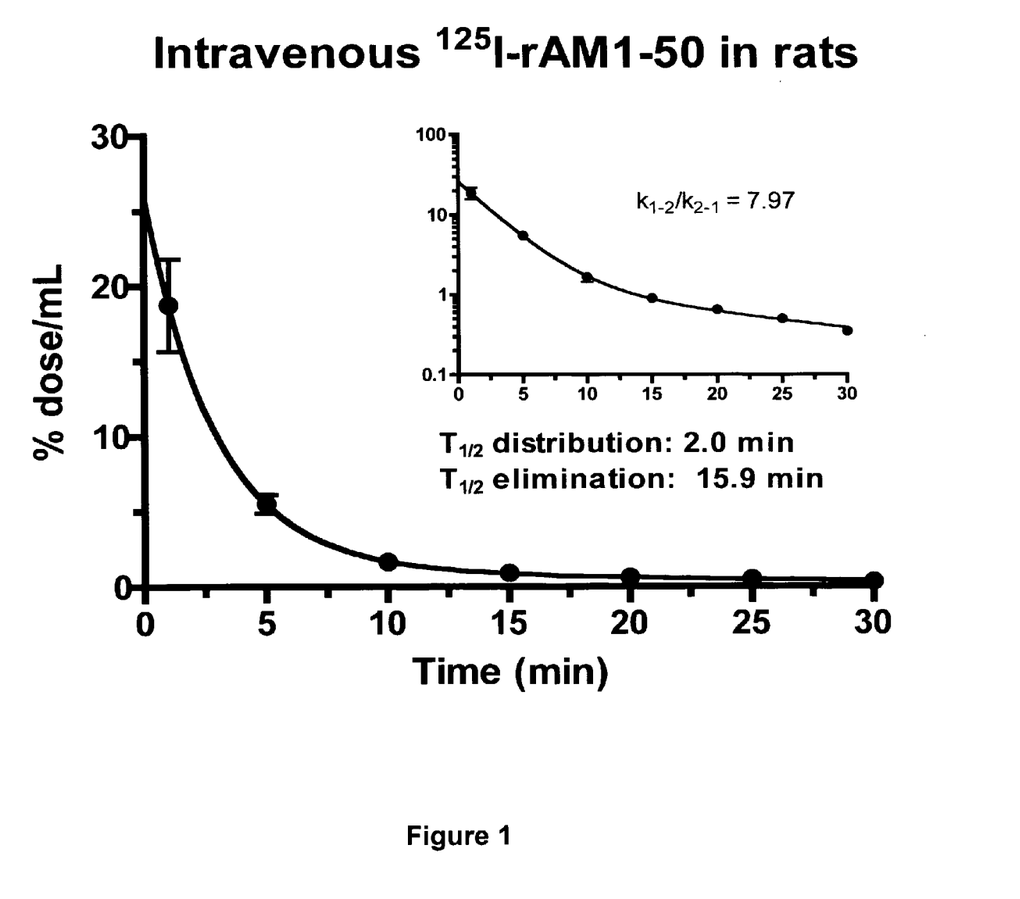
FIG. 1 illustrates the plasma kinetics of $^{125}$I-rAM(1-50) after a single intravenous injection in a rat.
Figure 2:
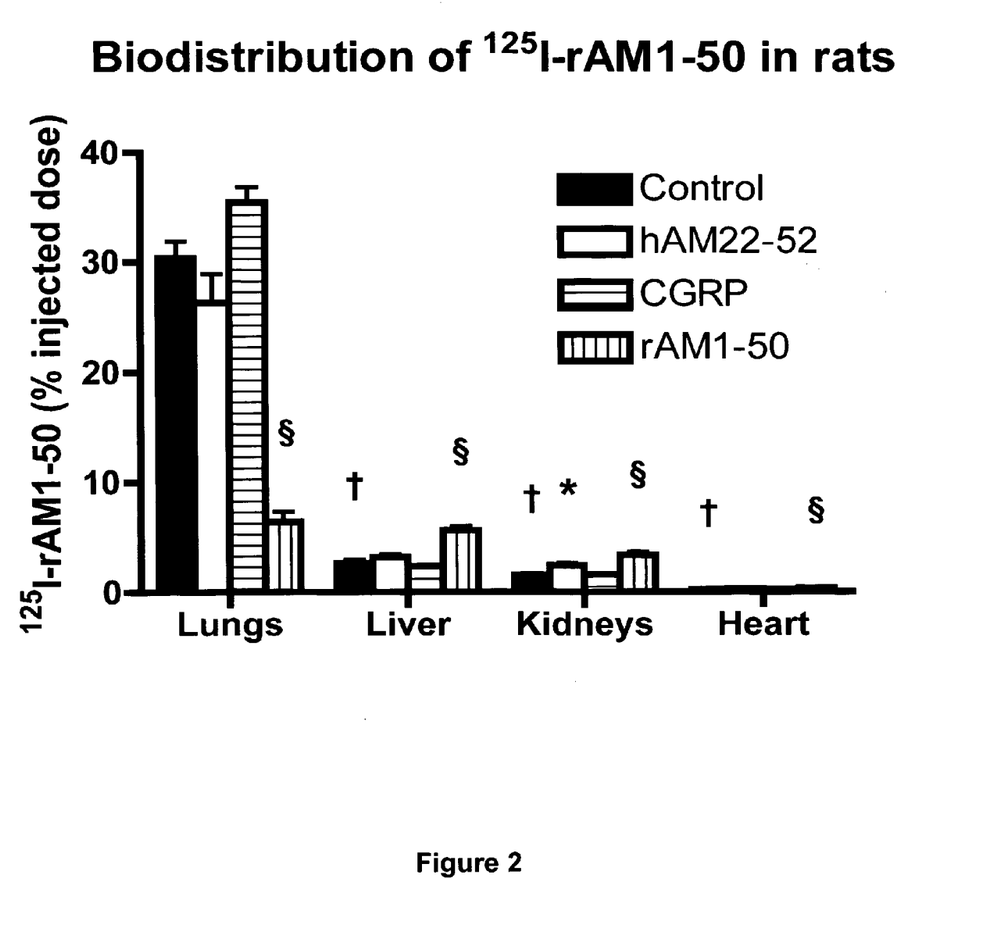
FIG. 2 illustrates the Biodistribution of $^{125}$I-rAM(1-50) after intravenous injection in rats († P<0.001 compared with the lungs; * P<0.005 and §compared with control, n=10/group)

Radiolabelled $^{125}$I-rAM(1-50) (Amersham Biosciences) ($^{125}$I labelled rat adrenomedullin) was injected in a volume of 200 µl (0.3 µmol, 0.5 µCi) either into the right heart chambers via the right jugular vein catheter (n=10), or in the systemic circulation via the carotid catheter (n=10). A series of 200 µl blood samples were collected 1 min after the initial AM injection, then repeated every 5 min for a 30-min period. After each collection, an equal volume of saline was injected into the animal to maintain blood volume and pressure. The animals were then killed and the lungs, liver, kidneys (en bloc with the adrenal glands) and heart were removed and gravity drained. The blood samples and organs were then placed in a gamma-counter (model 1470 Wizard; Wallac) to determine $^{125}$I radioactivity. Results are expressed as a percentage of total radioactivity injected. Results for these experiments are shown in FIGS. 1 and 2.

Effects of Antagonists on AM Clearance

Figure 3:
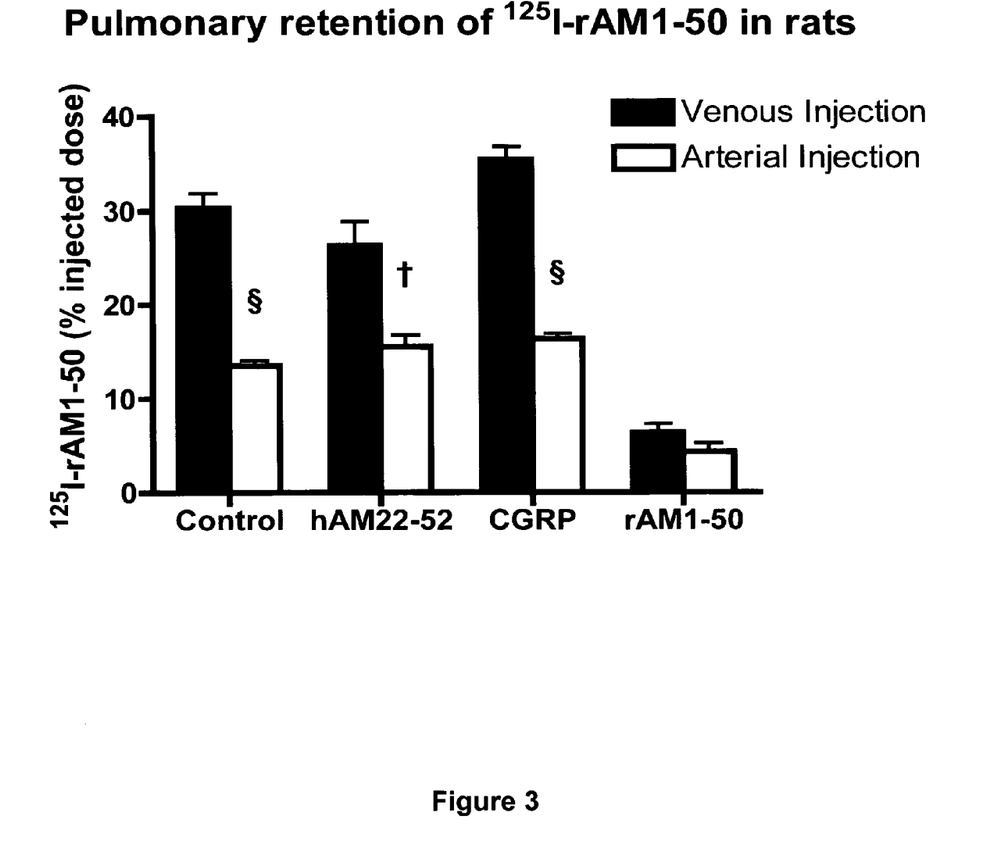
FIG. 3 illustrates the pulmonary retention of $^{125}$I-rAM(1-50) in rats after intravenous and intra-arterial injection († P<0.005 and §P<0.001 compared with venous injection, n=10/group)

Three groups of rats (n=20 in each) were studied and received either 200 μl of hAM(22-52) (5.6 nmol; Bachem), 100 μl of CGRP (1.75 nmol; Phoenix Pharmaceuticals) or 100 μl of unlabelled rAM(1-50) (17.5 nmol; American Peptide). The drugs were given by either intraarterial (n=10 in each group) or intravenous (n=10 in each group) injection 5 min before the $^{125}$I-rAM(1-50) bolus. Plasma samples and tissues were treated as described above. Results are shown in FIG. 3.

Measurement of Endogenous rAM(1-50) Levels in Plasma and Tissues

Plasma levels were measured in samples obtained at baseline as described above (n=40). In order to evaluate endogenous tissue levels, ten additional rats were studied. After being anaesthetized, the animals were killed by removal of the lungs, liver, kidneys and heart. Homogenization of organs was performed by adding 2 ml of buffer [4 mol/l guanidine thiocyanate (Fisher Scientific) and 1% trifluoroacetic acid (Sigma)] to 200 mg of tissue samples with the use of an automatic revolving pestle (DynaMix; Fisher Scientific). Homogenates were vortex-mixed and samples (100 μl) kept at 4 C for subsequent protein determination by Bradford analysis. Remaining samples were centrifuged at 1300 g (4 C) and the supernatant saved for processing. Tissues and plasma samples were extracted using Sep-Pak C18 cartridges (Waters) and irAM(1-50) was measured using a competitive RIA (Phoenix Pharmaceuticals) according to the manufacturer's instructions. The detection limit of this assay is approx. 4.7 pg/tube with a specificity for rAM(1-50) of 100%, without any cross reactivity (0%) with hAM(1-52), pro-hAM, pro-rAM, amylin and ET (endothelin)-1.

In Vivo Single-pass Measurement of AM Clearance in Dogs

Dogs were anaesthetized and prepared as described in detail in reference [13], which is hereby incorporated by reference. A catheter was inserted into the carotid artery and positioned just above the aortic valve. This catheter was connected to a peristaltic pump for automated blood withdrawal. Another catheter was placed into the jugular vein and positioned in the right ventricular outflow tract to allow bolus injection of the study tracers. A bolus was prepared by adding 3.3 μCi of 125I-rAM(1-50) (2.9 pmol) to 3 ml of Evans-Blue-dye labelled albumin and 0.9% saline to give a final volume of 6 ml. The mixture was separated into three equal parts for the two successive experiments in each animal and to realize dilution-curve standards. A baseline single-bolus indicator-dilution experiment was performed. After 5 min, CGRP (n=7), hAM(22-52) (n=8) and unlabelled rAM(1-50) (n=9) were administered as an intravenous bolus of 100 nmol and 5 min later a second indicator dilution experiment was performed.

Figure 4:
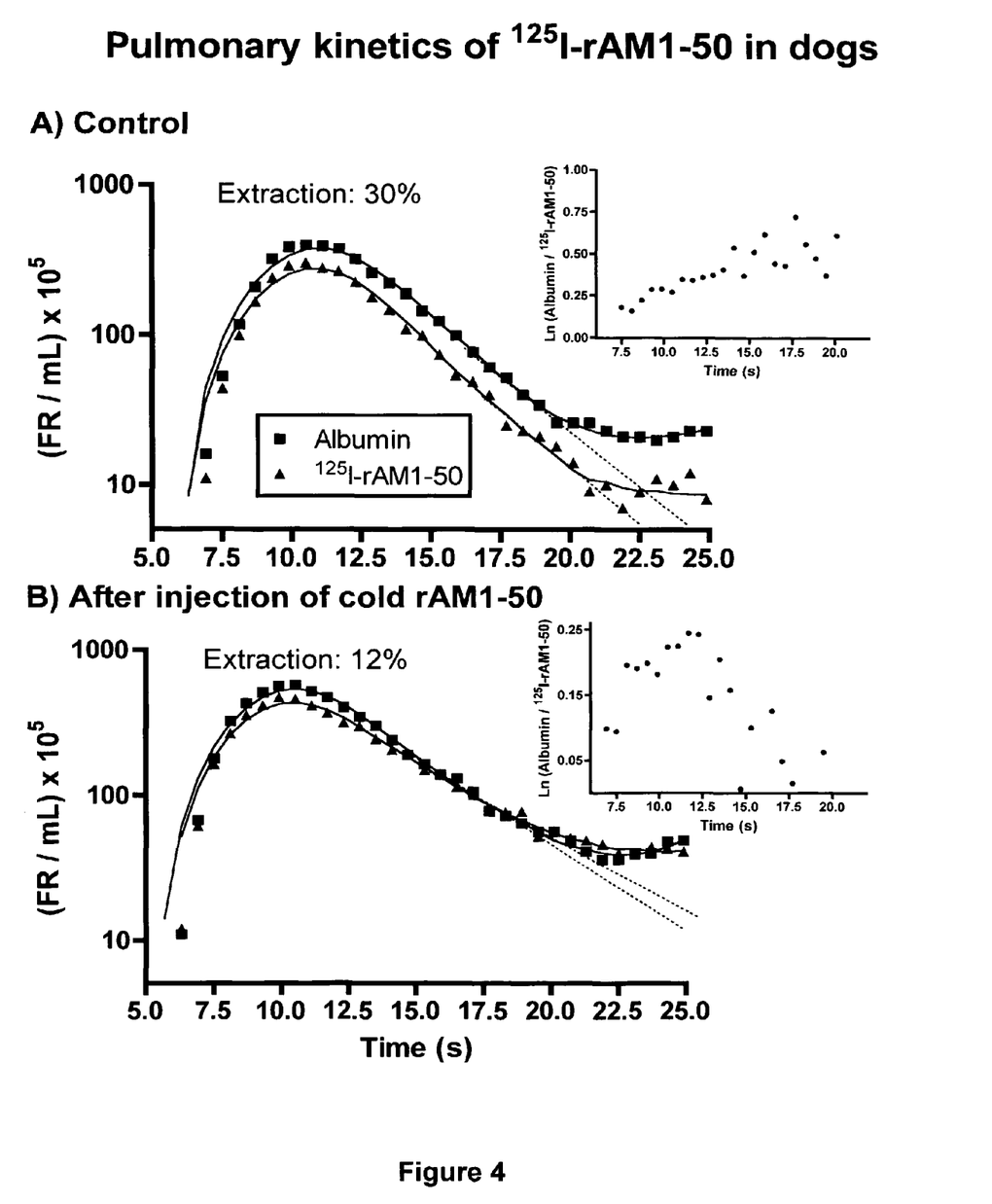
FIG. 4 illustrates an example of indicator-dilution curve outflow profiles in the canine pulmonary circulation in control conditions (A) and after injection of unlabelled rAM(1-50) (B), Insets showing the natural log ratio curves of the tracers (FR is fractional recovery of each tracer)

The collected samples were processed and indicator-dilution curves constructed and analyzed as described in previously cited reference 13. Cardiac output and mean tracer AM extraction during the pulmonary transit time were computed from the curves. Mean tracer extraction corresponded to the difference between the areas of the outflow curve of the vascular reference (albumin) and that of the extracted tracer (AM). Recirculation of the tracers apparent in the terminal portion of the curves was removed by linear extrapolation of the semi-logarithmic down slopes. Results are shown in FIG. 4.

Statistical Analysis

Multiple group comparisons were performed by factorial ANOVA, followed, when a significant interaction was found, by the Bonferroni/Dunn t test. Plasma kinetics of 125I-rAM (1-50) was fitted using a two-phase exponential decay equation with GraphPad Prism (version 4.0) software. Pulmonary clearance of 125I-AM(1-50) in rats after intravenous and intra-arterial injection was compared by two-tailed unpaired Student's t test. Comparison between venous and arterial rAM(1-50) levels in plasma was performed with a two-tailed paired Student's t test. In the canine experiments, the effect of drugs on AM extraction was analyzed by two-tailed paired Student's t tests. A P value of <0.05 was considered significant. All results are reported as means ±S.E.M.

Results

Kinetics of $^{125}$I-rAM(1-50) in Plasma

As shown in FIG. 1, intravenously administered $^{125}$IrAM (1-50) rapidly decreased following a two-compartment model with a relatively rapid distribution half-life of 2.0 min [95% Cl (confidence interval), 1.98-2.01] and an elimination half-life of 15.9 min (95% Cl, 15.0-16.9). Compartmental analysis revealed that the ratio of rate constants for exchange between the central and peripheral compartments ($k_{1-2}/k_{2-1}$) was relatively high at 7.97, demonstrating an important distribution of drug into the peripheral compartment. The volumes of distribution were computed, including the volume of the central compartment (Vc=3.84 ml), the volume at steady state (Vss=12.5 ml) and the apparent volume of distribution (Varea=35 ml). Administration of a human AM fragment (hAM(22-52)), CGRP or unlabelled rAM(1-50) prior to the injection of radiolabelled rAM(1-50) did not modify plasma kinetics, resulting in almost perfectly superimposable curves (results not shown).

Biodistribution of 125I-rAM(1-50) After Infection

As shown in FIG. 2, the lungs predominantly retained the peptide 30 min after the injected dose (P<0.001). There was proportionately only minor retention by the liver, kidneys and heart. Administration of hAM(22-52) and CGRP did not significantly modify this distribution, except in kidneys, where only hAM(22-52) elevated the retained activity (P<0.005). Injection of unlabelled rAM(1-50) caused an important reduction in lung activity (P<0.001) and significantly increased (P<0.001) the amount retained by the liver, kidneys and heart.

Lung Retention After Intravenous Compared with Intra-arterial Administration

In the control group (n=10 per injection site), there was evidence of important first-pass pulmonary retention with a more than 50% decline in the amount of the peptide retained after intra-arterial compared with intravenous injection (FIG. 3). This pulmonary first-pass retention was not affected by prior administration of hAM(22-52) or CGRP. However, pretreatment with rAM(1-50) did not decrease further the already lowered pulmonary retention after intra-arterial compared with intravenous injections.

Endogenous rAM(1-50) Levels in Plasma and Organs

There was no difference in irAM(1-50) levels in venous (3.1+−0.2 pmol/l) and arterial (3.2+−0.2 pmol/l) plasma (n=40). Tissue levels (n=10) were more than 20-fold higher in the lungs (249.0+−48.3 pg/mg protein; P<0.001) compared with liver (11.1+−1.3 pg/mg of protein), kidneys (11.7+−1.4 pg/mg of protein) and heart (7.2+−0.9 pg/mg of protein).

Single-Pass Pulmonary Kinetics of $^{125}$I-rAM(1-50) in Dogs In Vivo

Analysis of the indicator-dilution curve outflow profiles demonstrated a significant first-pass retention of $^{125}$IrAM(1-50). A typical experiment is shown in the FIG. 4(A). The curve for $^{125}$I-rAM(1-50) progressively deviated from its vascular reference (labelled albumin). The recirculation of tracers was removed by extrapolation of the semi-logarithmic down slopes. The difference between the areas of the two tracers' curves, which represent mean tracer $^{125}$I-rAM(1-50) extraction during a single pulmonary transit time, was 30% in that experiment. Plotting the natural log ratio of the two tracers characterized further the extraction over time (FIG. 4). The relationship was found to be linear, demonstrating that extraction increased over time with no evidence of return of the extracted peptide into circulation. In terms of ordinary capillary modeling, the slope of this relationship represents the sequestration rate constant for $^{125}$I-rAM(1-50) by the lungs. In the same animal, a second experiment was performed after injection of unlabelled rAM(1-50) (FIG. 4B). There was an evident reduction in pulmonary clearance with a smaller differential curve area compared with albumin (mean extraction 12%) and progressively converging curves on the down slope. The log ratio is completely modified with an initial plateau followed by a decrease, demonstrating the return of the tracer into the circulation.

Mean single-pass pulmonary extraction of $^{125}$IrAM(1-50) was 36.4±2.1%. This was significantly decreased (P<0.01) to 21.9±2.4% after the administration of unlabelled rAM(1-50). Extraction was not affected by CGRP with 44.6±2.9% occurring in the control compared with 40.6±2.9% after administration. There was a slight but significant (P<0.01) decrease in extraction with hAM(22-52) from 40.0±1.7% before to 31.4±3.3% after administration.

Discussion

In this study, plasma kinetics and biodistribution of exogenously administered AM in rats as well as plasma and tissue levels of endogenous AM were evaluated. Single-pass pulmonary clearance of AM in dogs using the indicator-dilution technique was further quantified and characterized in vivo.

Injected AM has a relatively short elimination half-life of 16 min with rapid and important distribution into a peripheral compartment. The lungs retain most of the injected activity with evidence of single-pass clearance, since retention is lower after intra-arterial compared with intravenous injection. There was no difference in total endogenous irAM levels across the pulmonary circulation with very high endogenous tissue levels also found in the lungs compared with other organs. These data demonstrate that the lungs are a major site for AM clearance, the absence of a gradient suggesting that the lungs also have the ability to produce and release AM into the circulation.

A relatively small volume of distribution for the central compartment (3.5 ml) was found, which is, in fact, less than the total blood volume of the rat. This is consistent with the very rapid clearance of AM from plasma with evidence of a first-pass effect into the pulmonary circulation. Thus a substantial proportion of intravenously injected AM is relatively rapidly cleared as it passes through the pulmonary circulation and does not distribute into the systemic circulation. The importance of a first-pass pulmonary clearance was confirmed and quantified by the use of the indicator-dilution experiments in dogs where it was found that approximately 36% of the injected AM was retained within the few seconds of a single pulmonary transit time. The outflow profile demonstrates that the retained AM is bound to its clearance site and does not return into the circulation. This, combined with the data in rats, would suggest that AM binds with relatively high affinity and relatively irreversibly to its receptor. This is consistent with previous data demonstrating important specific AM binding sites in the lungs of rats and humans [15,16], with maximum binding in the lungs being higher than in any other organ studied [16]. This profile is reminiscent of the potent vasoconstrictor ET-1, which is also predominantly cleared by the pulmonary circulation by the endothelial ETB receptor [13].

The effects of AM are mediated by at least two different receptors [17]. One is the CGRP receptor to which AM binds with low affinity, whereas the other is considered a specific AM receptor that can blocked by the C-terminal fragment of AM, hAM(22-52). In the present study, it was found that $^{125}$I-rAM(1-50) clearance by the lungs can be competitively inhibited by the administration of unlabelled rAM(1-50). Interestingly, however, unlabelled rAM(1-50) did not modify the plasma kinetics of the peptide, as we observed a compensatory increase in retention by the liver, kidney and heart. This supports further the important clearance role of the lungs and suggests that most of the injected unlabelled AM was also retained by the lungs, explaining the lack of inhibition in peripheral organs where levels of $^{125}$I-rAM(1-50) must have been higher than those of the unlabelled peptide. There was no effect of similar doses of CGRP, demonstrating that the CGRP receptor is not responsible for pulmonary clearance. Administration of the C-terminal fragment hAM(22-52) also did not modify pulmonary retention in rats, although it did cause a small significant increase in the kidneys. These results were confirmed by the in vivo indicator-dilution studies in dogs where we found important first-pass extraction of 125I-rAM(1-50) which was importantly reduced after injection of unlabelled rAM(1-50), slightly reduced after hAM(22-52) and unaffected by CGRP. Previous investigators have evaluated pulmonary clearance of AM in isolated rat lungs and pulmonary endothelial cells and found that AM levels in effluents and culture media were unchanged after CGRP, but increased after administration of hAM(22-52) [18]. The structural components of the CGRP and AM receptors, CRLR, RAMP1, RAMP2 and RAMP3 are all expressed in rat lungs [19]. Northern-blot analysis has revealed previously that RAMP2, which confers AM selectivity to the receptor, is highly expressed in rat lung tissues compared with RAMP1 and RAMP3 [20]. Using selective CRLR antibodies and immunohistochemistry, Hagner et al. [21,22] demonstrated intense staining in the alveolar capillaries of both humans and rats. These previous findings, together with the present study, suggest that lung AM clearance is mediated by specific AM receptors, possibly at the level of the pulmonary vascular endothelium.

Conclusions

The lung is a primary site for AM clearance. There is important first-pass pulmonary clearance of AM through specific receptors. This suggests that the lungs not only modulate circulating levels of this peptide, but also represent its primary target.

EXAMPLE 3

Pharmacokinetics of 99mTc Labelled AM and Imaging Using Same

Widely accessible in most nuclear medical centres via $^{99}$Mo/$^{99m}$Tc generator, technetium-99m shows suitable nuclear properties for nuclear imaging with γ-emitting of 140.5 keV and a short half-life of 6.01 h (34). To avoid strong perturbation of hAM1-52 chemical structure and, consequently, the loss of its biological properties during radiolabelling with $^{99m}$Tc, a successful procedure, called 'bifunctional approach', has been proposed. This strategy consists of tethering a strong chelating group for the radionuclide to a point of the peptide that is irrelevant for preserving its biological properties (23, 26, 31). Thus, we developed chelated radiolabelled adrenomedullin derivatives, preferably a chelated hAM1-52 derivative using diethylenetriaminepentaacetic acid (DTPA) radiolabelled with $^{99m}$Tc.

The present example was designed to systematically evaluate the biodistribution, pharmacokinetics and multi-organic clearance of $^{99m}$Tc-DTPA-hAM1-52 in dogs in vivo. Furthermore, the purpose of this investigation was to assess the utility of the radiolabelled peptide as a pulmonary vascular imaging agent.

Anesthesia and Animal Preparation

All experimental procedures were performed in accordance with regulations and ethical guidelines from Canadian Council for the Care of Laboratory Animals, and received approval by the animal ethics and research committee of the Montreal Heart Institute. Mongrel dogs weighing between 20-30 kg and presenting negative Dirofilaria imitis blood test results were anesthetized by an initial intravenous dose of pentobarbital sodium (50 mg/kg). Animals were intubated and mechanically ventilated using room air. Cutaneous electrocardiographic leads were installed, and 18F cathlon with three-way was installed on both saphenous vein for 0.9% sodium chloride perfusion, radiolabelled injection and blood collection. A right arterial femoral catheter was also inserted using the Seldinger technique for continuous blood pressure monitoring. Additional doses of pentobarbital sodium were used if noxious stimuli (pinching near the eye) could elicit nociceptive motor reflexes or changes of the systemic blood pressure.

Dogs (n=10) undergoing surgical procedures were anesthetized and prepared as previously described, but maintained ventilated with 1-3% isoflurane. Pulmonary lobectomy was obtained by performing a surgical ligature of the right median lobe of the lungs.

Pharmacokinetics of 99mTc-DTPA-hAM1-52 in Plasma

Figure 5:
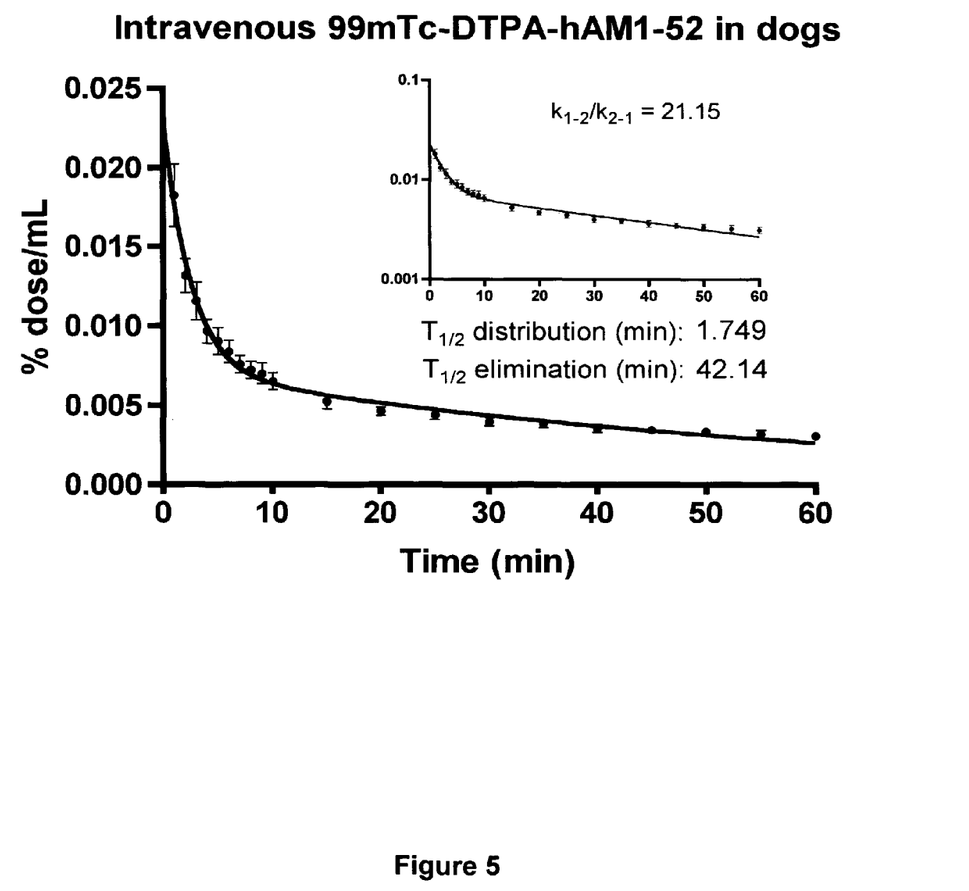
FIG. 5 illustrates the plasma kinetics of $^{99m}$Tc-DTPA-hAM1-52 after single intravenous injections in dogs, the data being fitted with a two-phase exponential decay equation (the inset shows a logarithmic scale, n=6/group)

Purified and buffered $^{99m}$Tc-DTPA-hAM1-52 samples were injected in right saphenous vein (n=6). A series of 2 mL blood samples were collected 1 min after the initial AM injection for a 10-min period, then repeated every 5 min for the following 50-min period. Blood samples were taken via left saphenous vein. After each collection, an equal volume of saline was injected into the animal to maintain blood volume and pressure. The blood samples were then placed in an automatic gamma counter (model 1272 Clinigamma, LKB Wallac, Finland) to determine $^{99m}$Tc activity. Results were expressed as a percentage of total radioactivity injected per mL and are shown in FIG. 5.

Biodistribution of 99mTc-DTPA-hAM1-52 and Multi-Organic Clearance In Vivo

Figure 6:
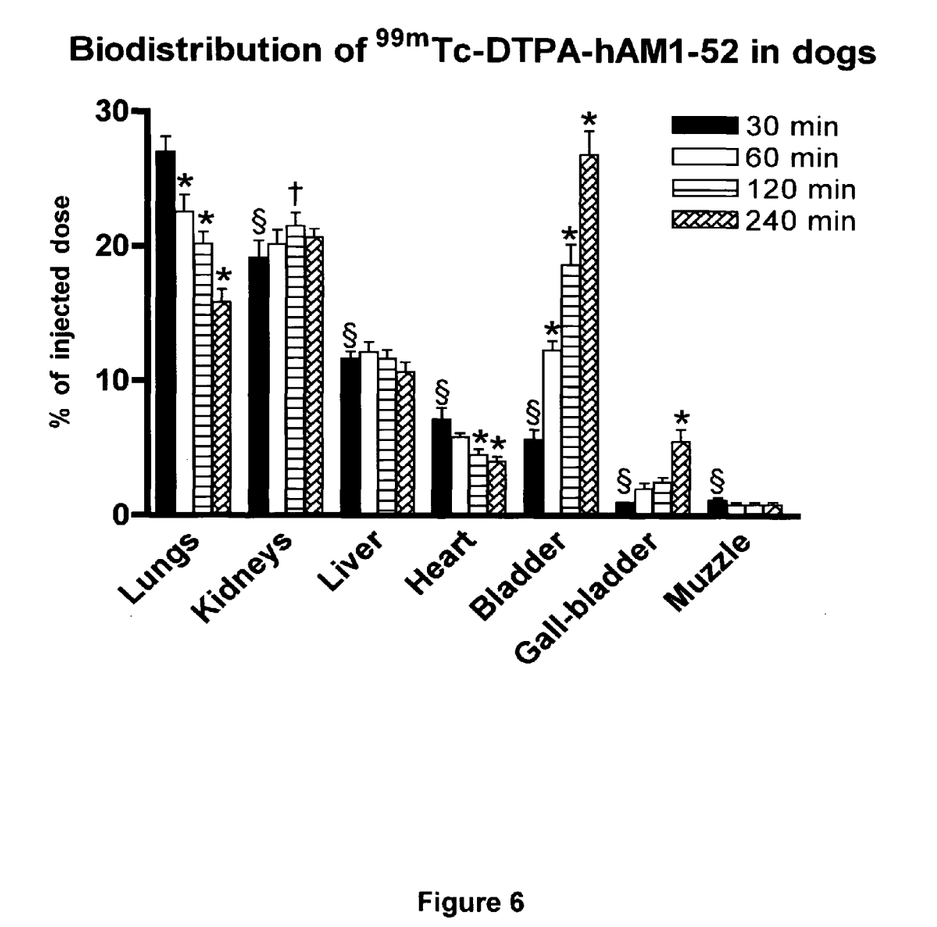
FIG. 6 illustrates the biodistribution of $^{99m}$Tc-DTPA-hAM1-52 after intravenous injection in dogs (†P<0.005 vs. 30 minutes; *P<0.001 vs. 30 minutes; §P<0.001 vs. lungs, n=6/group)
Figure 7:
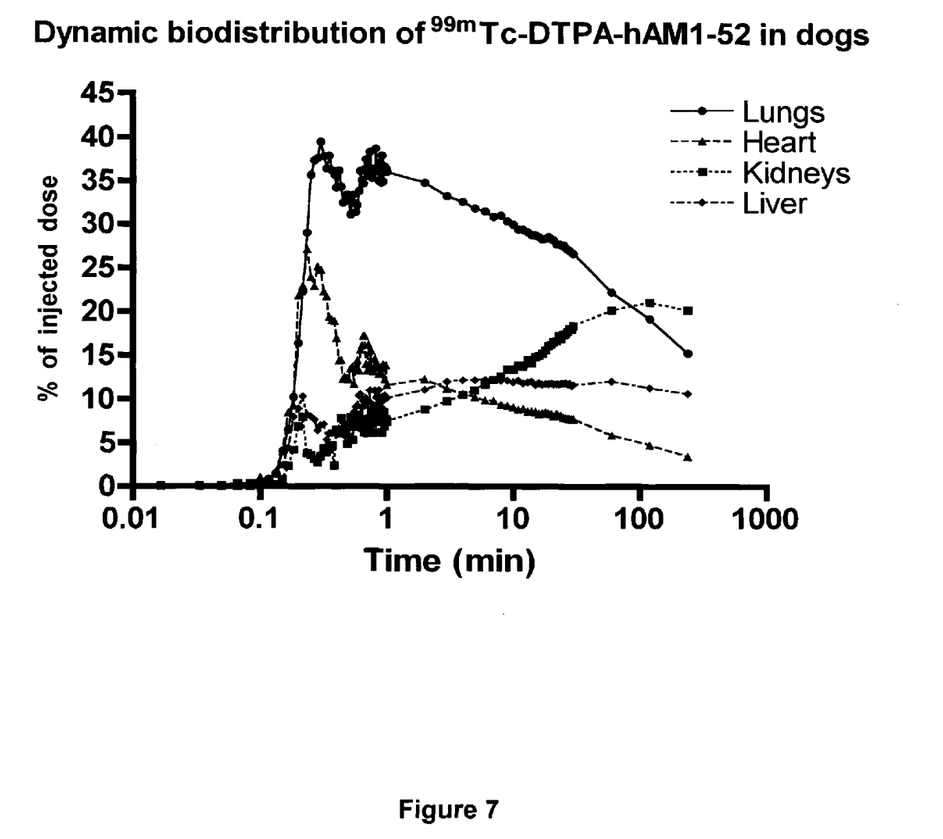
FIG. 7 illustrates the dynamic biodistribution of $^{99m}$Tc-DTPA-hAM1-52 after intravenous injection in dogs (n=6/group)

Multi-organic biodistribution of $^{99m}$Tc-DTPA-hAM1-52 was evaluated with an Anger camera (420/550 Mobile Radioisotope Gamma Camera; Technicare, Solon, Ohio, USA) equipped with on board computer, and a low-energy parallel-hole collimator (model 14S22014). Following intravenous injection of $^{99m}$Tc-DTPA-hAM1-52, dynamic acquisition of the lungs, heart, liver and kidneys was recorded for a 30-min period (one frame/sec during the first minute, then one frame/min for the remaining time). Static acquisitions was also recorded for whole individual organs, including lungs, kidneys, liver, heart, bladder, gallbladder and muzzle, at 30, 60, 120, 240 minutes after initial injection. These recordings were performed both in ventral and dorsal positions. Results are shown in FIGS. 6 and 7.

Gamma Camera Results Analysis

Figure 8:
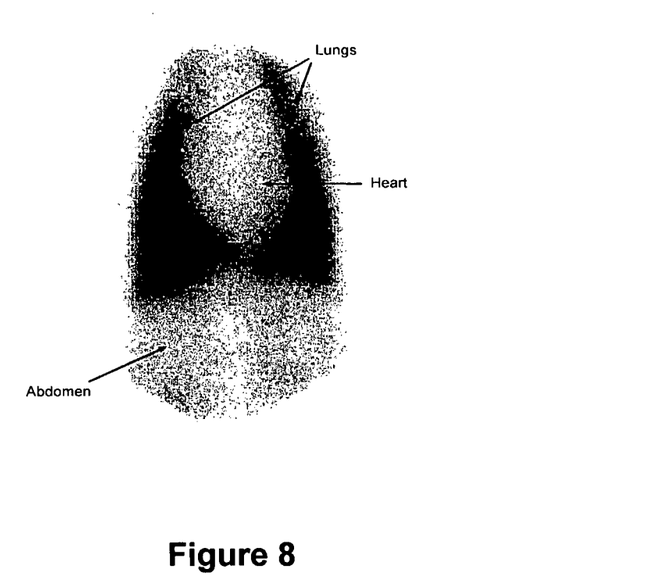
FIG. 8 is a gamma camera image of a dog's thorax obtained further to an injection of $^{99m}$TC marked AM.
Figure 9:
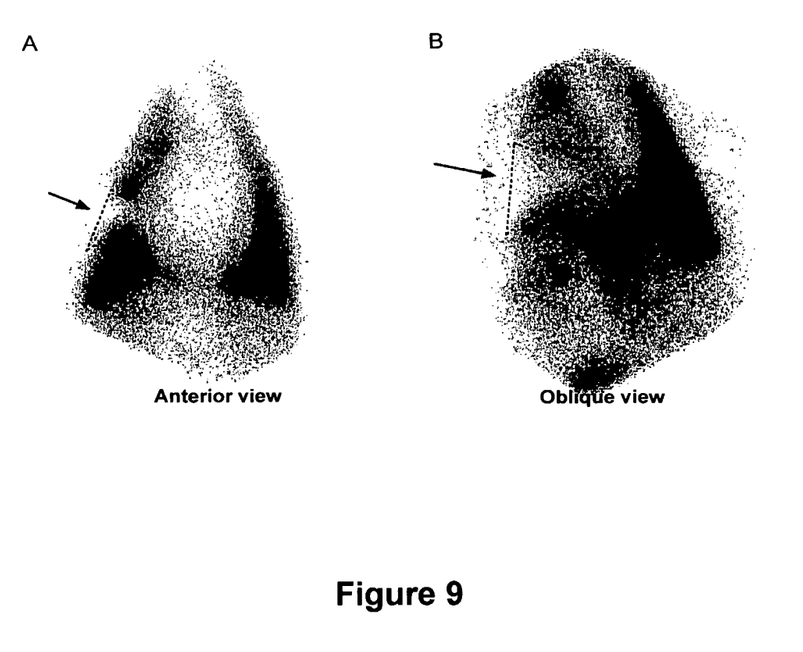
FIG. 9 illustrates selective surgical pulmonary lobectomy effects on $^{99m}$Tc-DTPA-hAM1-52 perfusion in dog as imaged through a gamma camera: (A) anterior view, (B) oblique view, a wedge shaped perfusion defect being indicated by an arrow and delimitated by dotted lines.

Dynamic and static acquisitions were evaluated by using Matlab version 7.01 image analysis tools software. The $^{99m}$Tc total count, $^{99m}$Tc mean count, and region of interest (ROI) size were calculated for each organ. Data correction was applied for 1) radioactive decay, 2) surgical table attenuation (dorsal images only), 3) geometric mean, and 4) organ's attenuation based on transmission factor. Results were expressed as a percentage of total radioactivity injected and examples of images obtained are shown in FIGS. 8 and 9.

Statistical Analysis

Plasma kinetics of $^{99m}$Tc-DTPA-hAM1-52 was fitted using a two-phase exponential decay equation with GraphPad Prism version 4.0 software. Time effects on each organ biodistribution were analyzed by two-way repeated measures ANOVA followed, when a significant interaction was found, by Bonferroni/Dunn t-test. Multiple organs biodistribution comparison at 30 minutes was performed by one-way ANOVA followed, when a significant interaction was found, by Bonferroni/Dunn t-test. A P values of <0.05 was considered significant. All results are reported as mean ±S.D.

Results

Kinetics of $^{99m}$Tc-DTPA-hAM1-52 in Plasma (FIG. 5)

Intravenously administered $^{99m}$Tc-DTPA-hAM1-52 decreased relatively rapidly following a two-compartment model with a relatively rapid distribution half-life of 1.75 min (95% confidence interval, Cl: 1.31-2.65) and an elimination half-life of 42.14 min (Cl: 30.41-68.63). Compartmental analysis reveals that the ratio of rate constant for exchange between the central and peripheral compartments ($k_{1-2}/k_{2-1}$) is relatively high at 24.09, demonstrating an important distribution of drug into the peripheral compartment.

Biodistribution of $^{99m}$Tc-DTPA-hAM1-52 After Injection (FIG. 6)

The lungs predominantly retained the peptide with 27.00±2.76% of the injected dose after 30 minutes (P<0.001), as compared to kidneys (19.17±3.06%), liver (11.67±1.37%), heart (7.17±2.04%), bladder (5.67±1.75%), gallbladder (0.96±0.38%), and muzzle (1.17±0.41%). Lung retention was mildly reduced with time but sustained up to 4 hours after the injection (15.83±2.32%). Furthermore, uptake progressively increased in the bladder (26.83±4.36%) and gallbladder (0.83±0.41%), consequently to the excretion of the radiolabelled peptide. The $^{99m}$Tc-DTPA-hAM1-52 biodistribution in the kidneys, liver, and muzzle remained unchanged with time, with respectively 20.67±1.51%, 10.67±1.75%, and 0.83±0.41% at 240 minutes after peptide injection.

Dynamic Biodistribution $^{99m}$Tc-DTPA-hAM1-52 After Injection (FIG. 7)

Analysis of dynamic multi-organic biodistribution demonstrates significant pulmonary first pass retention of $^{99m}$Tc-DTPA-hAM1-52. The curve for lungs clearance also shows recirculation of the radiolabelled peptide, followed by a slow decrease with time. Moreover, heart curve indicates similar first pass retention of $^{99m}$Tc-DTPA-hAM1-52, without however sustained clearance with time. On the opposite, liver and kidneys dynamic biodistribution demonstrate only slow but continuous retention with time.

Selective Pulmonary Lobectomy Effects on $^{99m}$Tc-DTPA-hAM1-52 Perfusion (FIGS. 8 and 9)

Homogeneous distribution of the tracer is evident in the lungs of a normal animal (FIG. 8) with substantially no detectable activity over the region of the heart and little activity in the abdomen. This allows for good lung imaging without significant contaminant activity from surrounding organs. After surgical lobectomy mimicking the pathologic condition of a pulmonary embolus (FIG. 9), there is an evident perfusion defect which allows the diagnosis by external imaging. FIG. 9 shows images obtained through anterior (panel A) and oblique (panel B) views. The perfusion defect was substantially wedge-shaped. This defect is indicated by an arrow and substantially delimitated by dotted lines Although the present invention has been described hereinabove by way of preferred embodiments thereof, it can be modified, without departing from the spirit and nature of the subject invention as defined in the appended claims.

All references cited and/or discussed in this specification are incorporated herein by reference in their entirety and to the same extent as if each reference was individually incorporated by reference.

The in vivo experiments in rats and dogs, as described in the specification, may be predictive of biological effects in humans or other mammals and/or may serve as animal models for use of the present invention in humans or other mammals.

REFERENCES

1. Kitamura, K., Sakata, J., Kangawa, K., Kojima, M., Matsuo, H. and Eto, T. (1994) Cloning and characterization of cDNA encoding a precursor for human adrenomedullin. Biochem. Biophys. Res. Commun. 194, 720-725
2. Sugo, S., Minamino, N., Kangawa, K. et al. (1994) Endothelial cells actively synthesize and secrete adrenomedullin. Biochem. Biophys. Res. Commun. 201, 1160-1166
3. Hinson, J. P., Kapas, S. and Smith, D. M. (2000) Adrenomedullin, a multifunctional regulatory peptide. Endocr. Rev. 21, 138-167
4. Hay, D. L. and Smith, D. M. (2001) Receptors: molecular identity and function. Peptides 22, 1753-1763
5. Kuwasako, K., Kitamura, K., Ito, K. et al. (2001) The seven amino acids of human RAMP2 (86) and RAMP3 (59) are critical for agonist binding to human adrenomedullin receptors. J. Biol. Chem. 276, 49459-49465
6. Poyner, D. R., Sexton, P. M., Marshall, I. et al. (2002) International Union of Pharmacology. XXXII. The mammalian calcitonin gene-related peptides, adrenomedullin, amylin, and calcitonin receptors. Pharmacol. Rev. 54, 233-246
7. Eguchi, S., Hirata, Y., Iwasaki, H. et al. (1994) Structure-activity relationship of adrenomedullin, a novel vasodilatory peptide, in cultured rat vascular smooth muscle cells. Endocrinolog 135, 2454-2458
8. Sabates, B., Granger, T., Choe, E. et al. (1996) Adrenomedullin is inactivated in the lungs of neonatal piglets. J. Pharm. Pharmacol. 48, 578-580
9. Hirayama, N., Kitamura, K., Imamura, T., Kato, J., Koiwaya, Y. and Eto, T. (1999) Secretion and clearance of the mature form of adrenomedullin in humans. Life Sci. 64, 2505-2509
10. Nishikimi, T., Kitamura, K., Saito, Y. et al. (1994) Clinical studies on the sites of production and clearance of circulating adrenomedullin in human subjects. Hypertension 24, 600-604
11. Nishikimi, T., Matsuoka, H., Shimada, K., Matsuo, H. and Kangawa, K. (2004) Production and clearance sites of two molecular forms of adrenomedullin in human plasma. Am. J. Hypertens. 13, 1032-1034
12. Nishikimi, T., Nagata, S., Sasaki, T. et al. (2001) The active molecular form of plasma adrenomedullin is extracted in the pulmonary circulation in patients with mitral stenosis: Possible role of adrenomedullin in pulmonary hypertension. Clin. Sci. 100, 61-66
13. Dupuis, J., Goresky, C. A. and Fournier, A. (1996) Pulmonary clearance of circulating endothelin-1 in dogs in vivo: Exclusive role of ETB receptors. J. Appl. Physiol. 81, 1510-1515
14. Kitamura, K., Kato, J., Kawamoto, M. et al. (1998) The intermediate form of glycine-extended adrenomedullin is the major circulating molecular form in human plasma. Biochem. Biophys. Res. Commun. 244, 551-555
15. Martinez, A., Miller, M. J., Catt, K. J. and Cuttitta, F. (1997) Adrenomedullin receptor expression in human lung and in pulmonary tumors. J. Histochem. Cytochem. 45, 159-164
16. Owji, A. A., Smith, D. M., Coppock, H. A. et al. (1995) An abundant and specific binding site for the novel vasodilator adrenomedullin in the rat. Endocrinology 136, 2127-2134
17. Poyner, D. R. (1997) Molecular pharmacology of receptors for calcitonin-gene-related peptide, amylin and adrenomedullin. Biochem. Soc. Trans. 25, 1032-1036
18. Dschietzig, T., Azad, H. A., Asswad, L., Bohme, C., Bartsch, C. and Baumann, G. (2002) The adrenomedullin receptor acts as clearance receptor in pulmonary circulation. Biochem. Biophys. Res. Commun. 294, 315-318
19. Qing, X., Svaren, J. and Keith, I. M. (2001) mRNA expression of novel CGRP1 receptors and their activity-modifying proteins in hypoxic rat lung. Am. J. Physiol. Lung Cell. Mol. Physiol. 280, L547-L554
20. Nagae, T., Mukoyama, M., Sugawara, A. et al. (2000) Rat receptor-activity-modifying proteins (RAMPs) for adrenomedullin/CGRP receptor: cloning and upregulation in obstructive nephropathy. Biochem. Biophys. Res. Commun. 270, 89-93
21. Hagner, S., Haberberger, R., Hay, D. L. et al. (2003) Immunohistochemical detection of the calcitonin receptor-like receptor protein in the microvasculature of rat endothelium. Eur. J. Pharmacol. 481, 147-151
22. Hagner, S., Stahl, U., Knoblauch, B., McGregor, G. P. and Lang, R. E. (2002) Calcitonin receptor-like receptor:identification and distribution in human peripheral tissues. Cell Tissue Res. 310, 41-50
23. Dilworth, J. R. and S. J. Parrott (1998). "The biomedical chemistry of technetium and rhenium." Chem. Soc. Rev. 27: 43-55.
24. Dupuis, J., A. Caron, et al. (2005). "Biodistribution, plasma kinetics and quantification of single pass pulmonary clearance of adrenomedullin." Clin Sci 1:1.
25. Hinson, J. P., S. Kapas, et al. (2000). "Adrenomedullin, a multifunctional regulatory peptide." Endocr Rev 21(2): 138-67.
26. Hirayama, N., K. Kitamura, et al. (1999). "Secretion and clearance of the mature form of adrenomedullin in humans." Life Sci 64(26): 2505-9.
27. Hom, R. K. and J. A. Katzenellenbogen (1997). "Technetium-99m-labelled receptor-specific small-molecule radiopharmaceuticals: recent developments and encouraging results." Nucd Med Biol 24(6): 485-98.
28. Kitamura, K., J. Sakata, et al. (1993). "Cloning and characterization of cDNA encoding a precursor for human adrenomedullin." Biochem Biophys Res Commun 194(2): 720-5.

29. Liu, S. and D. S. Edwards (1999). "99mTc-Labelled Small Peptides as Diagnostic Radiopharmaceuticals." Chem Rev 99(9): 2235-68.
30. Nishikimi, T., K. Kitamura, et al. (1994). "Clinical studies on the sites of production and clearance of circulating adrenomedullin in human subjects." Hypertension 24(5): 600-4.
31. Nishikimi, T., H. Matsuoka, et al. (2000). "Production and clearance sites of two molecular forms of adrenomedullin in human plasma." Am J Hypertens 13(9): 1032-4.
32. Nishikimi, T., S. Nagata, et al. (2001). "The active molecular form of plasma adrenomedullin is extracted in the pulmonary circulation in patients with mitral stenosis: possible role of adrenomedullin in pulmonary hypertension." Clin Sci (Lond) 100(1): 61-6.
33. Schwochau, K. (2000). Technetium, Chemistry and Radiopharmaceutical Applications. Weinheim, Germany.
34. Sugo, S., N. Minamino, et al. (1994). "Endothelial cells actively synthesize and secrete adrenomedullin." Biochem Biophys Res Commun 201(3): 1160-6.
35. Forest, M. & Fournier, A.: BOP reagent for the coupling of pGlu and Boc His (Tos) in solid phase peptide synthesis. International Journal of Peptide and Protein Research, 1990; 35: 89-94

What is claimed is:

1. An adrenomedullin derivative comprising: an adrenomedullin peptide comprises the sequence: Tyr-Arg-Gln-Ser-Met-Asn-Asn-Phe-Gln-Gly-Leu-Arg-Ser-Phe-Gly-Cys-Arg-Phe-Gly-Thr-Cys-Thr-Val-Gln-Lys-Leu-Ala-His-Gln-Ile-Tyr-Gln-Phe-Thr-Asp-Lys-Asp-Lys-Asp-Asn-Val-Ala-Pro-Arg-Ser-Lys-Ile-Ser-Pro-Gln-Gly-Tyr (SEQ ID NO:1) or a fragment thereof chelated to at least one active agent by a chelating agent, wherein said active agent is selected from a paramagnetic element and a radioactive element, and said adrenomedulin derivative is configured for clinical imaging of the pulmonary circulation of a live mammal.

2. The adrenomedullin derivative of claim 1, wherein said radioactive element is selected from: $^{99m}$Tc, $^{67}$Ga, $^{64}$Cu, $^{90}$Y, $^{161}$Tb $^{177}$Lu, and $^{111}$In.

3. The adrenomedullin derivative of claim 1, wherein said chelating agent is selected from: diethylenetriaminepentaacetic acid (DTPA), 1,4,7,10-tetraazacyclododecan-N,N',N'',N'''-tetraacetic acid (DOTA), 1,4,8,11-tetraazacyclotetradecane-N,N',N'',N'''-tetraacetic acid (TETA), 6-hydrazinonicotinamide (HYNIC), desferioxamine and N,N',N''-tris(2-pyridylmethyl)-cis-1,3,5-triaminocyclohexane (tachpyr).

4. The adrenomedullin derivative of claim 3, wherein said radioactive element is $^{99m}$Tc and said chelating agent is DTPA.

5. The adrenomedullin derivative of claim 1, wherein said active agent comprises an element selected from: Fe, Ca, Mn, Mg, Cu, and Zn.

6. The adrenomedullin derivative of claim 5, wherein said chelating agent is selected from: desferioxamine and N,N',N''-tris(2-pyridylmethyl)cis-1,3,5-triaminocyclohexane (tachpyr).

7. The adrenomedullin derivative of claim 1, wherein said active agent is $^{99m}$Tc and said chelating agent is tachpyr.

8. The adrenomedullin derivative of claim 1, wherein said active agent is $^{99m}$Tc and said chelating agent is tachpyr.

9. The adrenomedullin derivative of claim 1, wherein said adrenomedulin derivative is configured for imaging vascular defects in said pulmonary circulation.

10. The adrenomedullin derivative of claim 1, wherein said adrenomedulin derivative is configured for functional imaging of the pulmonary circulation and detection of vascular perfusion abnormalities.

11. The adrenomedullin derivative of claim 1, wherein said adrenomedulin derivative is configured for detecting the presence or absence of pulmonary embolus.

12. The adrenomedullin derivative of claim 1, wherein said mammal is human.

13. The adrenomedullin derivative of claim 1 where said active agent is $^{64}$Cu and said chelating agent is DOTA.

14. The adrenomedullin derivative of claim 1 where said active agent is $^{99m}$TC and said chelating agent is DTPA.

* * * * *